(12) United States Patent
Regnier et al.

(10) Patent No.: US 9,068,995 B2
(45) Date of Patent: Jun. 30, 2015

(54) METHOD FOR DETERMINING DERIVATIZED ANALYTES IN A SEPARATED BIOLOGICAL FLUID

(71) Applicant: Novilytic, LLC, North Webster, IN (US)

(72) Inventors: Fred Regnier, West Lafayette, IN (US); Jinhee Kim, West Lafayette, IN (US); Jiri Adamec, Denton, NE (US); Timothy E. Woenker, Fort Wayne, IN (US); Richard P. Zoltek, Columbia City, IN (US); Wenchu Yang, Morton Grove, IL (US)

( * ) Notice: Subject to any disclaimer, the term of this patent is extended or adjusted under 35 U.S.C. 154(b) by 3 days.

(21) Appl. No.: 13/833,402

(22) Filed: Mar. 15, 2013

(65) Prior Publication Data

US 2014/0273260 A1 Sep. 18, 2014

(51) Int. Cl.
*G01N 33/82* (2006.01)
*G01N 33/50* (2006.01)
*G01N 33/00* (2006.01)

(52) U.S. Cl.
CPC .............. *G01N 33/82* (2013.01); *Y10T 436/24* (2015.01); *Y10T 436/203332* (2015.01); *G01N 2458/15* (2013.01); *G01N 2560/00* (2013.01)

(58) Field of Classification Search
CPC ....... G01N 31/22; G01N 33/82; G01N 33/98; G01N 31/00; G01N 33/50; G01N 33/48; G01N 33/00; C07C 233/82; C07C 233/98; C07C 233/81; C07C 233/64; Y10T 436/24; Y10T 436/20; Y10T 436/203332; Y10T 436/00
USPC .......................................... 436/131, 127, 174
See application file for complete search history.

(56) References Cited

U.S. PATENT DOCUMENTS

| | | | |
|---|---|---|---|
| 5,266,219 A | 11/1993 | Pall et al. | |
| 2014/0154700 A1* | 6/2014 | Teng et al. | 435/7.9 |

FOREIGN PATENT DOCUMENTS

| | | | | |
|---|---|---|---|---|
| WO | WO2004/072647 A1 * | 8/2004 | | G01N 33/68 |
| WO | WO2009/134439 | * 11/2009 | | G01N 33/00 |
| WO | 2011/072152 A1 | 6/2011 | | |

* cited by examiner

*Primary Examiner* — Christine T Mui

(57) ABSTRACT

The present invention comprises methods for determining the presence, amount, or concentration of analytes of interest including Vitamin D and other secosteroids from biological samples, through derivatization, with improved speed and ease of analysis and improved sensitivity to mass spectrometry. In a preferred embodiment, the present invention comprises methods for determining the presence, amount, or concentration of analytes of interest, including Vitamin D and other secosteroids from whole human blood, through derivatization, and using a plasma collection device to facilitate collection, separation, and preparation of the sample for derivatization and analysis.

49 Claims, 9 Drawing Sheets

| Donor 1 (fingerstick) | Analyte Peak Area (counts) | IS Peak Area (counts) | Formula #1 | d6-25OHVD3 (pg on collection disc) | Measured 25OHVD3 (ng/ml) | | |
|---|---|---|---|---|---|---|---|
| PSD replicate 1 | 5.07E+03 | 2.63E+03 | 1.93 | 28 | 22.52 | | |
| PSD replicate 2 | 6.00E+03 | 2.74E+03 | 1.82 | 28 | 21.23 | Average (ng/ml) | %RSD |
| PSD replicate 3 | 5.11E+03 | 2.89E+03 | 1.77 | 28 | 20.65 | 21.47 | 4.4 |
| Donor 1 (100μL plasma) | Analyte Peak Area (counts) | IS Peak Area (counts) | Formula #1 | d6-25OHVD3 (pg in a tube) | Measured 25OHVD3 (ng/ml) | | |
| LLE replicate 1 | 2.83E+05 | 8.83E+04 | 3.20 | 700 | 22.40 | | |
| LLE replicate 2 | 2.79E+05 | 8.88E+04 | 3.14 | 700 | 21.98 | Average (ng/ml) | %RSD |
| LLE replicate 3 | 3.52E+05 | 1.08E+05 | 3.26 | 700 | 22.82 | 22.40 | 1.9 |

FIGURE 4

| 25OHVD2/25OHVD3 d6-25OHVD2/d6-25OHVD3(internal standard) | 25OHVD2 Analyte Peak Area (counts) | d6-25OHVD2 IS Peak Area (counts) | 25OHVD2/d6-25OHVD2 Ratio | 25OHVD2/d6-25OHVD2 Average ratio | 25OHVD3 Analyte Peak Area (counts) | d6-25OHVD3 IS Peak Area (counts) | 25OHVD3/d6-25OHVD3 Ratio | 25OHVD3/d6-25OHVD3 Average ratio |
|---|---|---|---|---|---|---|---|---|
| 1/2pg | 7.43E+02 | 4.87E+02 | 1.52E+00 |  | 1.12E+03 | 1.18E+03 | 9.49E-01 |  |
| 1/2pg | 6.89E+02 | 5.30E+02 | 1.30E+00 |  | 1.05E+03 | 1.12E+03 | 9.35E-01 |  |
| 1/2pg | 4.81E+02 | 5.72E+02 | 8.40E-01 | 1.15E+00 | 1.23E+03 | 1.31E+03 | 9.41E-01 | 9.42E-01 |
| 2/4pg | 1.28E+03 | 1.09E+03 | 1.19E+00 |  | 2.14E+03 | 2.08E+03 | 1.03E+00 |  |
| 2/4pg | 1.04E+03 | 7.89E+02 | 1.32E+00 |  | 1.47E+03 | 2.04E+03 | 7.21E-01 |  |
| 2/4pg | 1.18E+03 | 1.09E+03 | 1.04E+00 | 1.19E+00 | 2.05E+03 | 2.08E+03 | 9.87E-01 | 9.13E-01 |
| 5/10pg | 2.53E+03 | 2.07E+03 | 1.22E+00 |  | 4.50E+03 | 4.63E+03 | 9.73E-01 |  |
| 5/10pg | 2.44E+03 | 2.29E+03 | 1.07E+00 |  | 4.93E+03 | 5.45E+03 | 9.05E-01 |  |
| 5/10pg | 2.63E+03 | 2.73E+03 | 9.64E-01 | 1.08E+00 | 6.22E+03 | 6.20E+03 | 1.00E+00 | 9.60E-01 |
| 10/20pg | 5.09E+03 | 4.86E+03 | 1.05E+00 |  | 1.19E+04 | 1.09E+04 | 1.01E+00 |  |
| 10/20pg | 5.39E+03 | 5.78E+03 | 9.32E-01 |  | 1.11E+04 | 1.03E+04 | 1.08E+00 |  |
| 10/20pg | 5.24E+03 | 5.47E+03 | 9.53E-01 | 9.80E-01 | 1.05E+04 | 1.09E+04 | 9.61E-01 | 1.02E+00 |
| 20/40pg | 1.02E+04 | 1.04E+04 | 9.77E-01 |  | 2.13E+04 | 2.10E+04 | 1.01E+00 |  |
| 20/40pg | 1.01E+04 | 1.32E+04 | 7.63E-01 |  | 2.03E+04 | 1.88E+04 | 1.08E+00 |  |
| 20/40pg | 1.06E+04 | 9.42E+03 | 1.13E+00 | 9.55E-01 | 2.05E+04 | 1.83E+04 | 1.12E+00 | 1.07E+00 |

FIGURE 6

METHOD FOR DETERMINING DERIVATIZED ANALYTES IN A SEPARATED BIOLOGICAL FLUID

STATEMENT REGARDING FEDERALLY SPONSORED RESEARCH OR DEVELOPMENT

The present invention was made with government support under Grant No. 1R43GM97798-1, awarded by the National Institutes of Health (NIH). The Government has certain rights in this invention.

CROSS-REFERENCES TO RELATED APPLICATIONS

None

BACKGROUND

Vitamin D (VD) is a vital substance for human survival that plays an important role in calcium and phosphorus absorption and bone mobilization. Vitamin D is either produced in human skin in a form known as Vitamin $D_3$ (cholecalciferol, $VD_3$) or it is absorbed from the diet, in a form known as Vitamin $D_2$ (ergocalciferol, $VD_2$). Both $VD_3$ and $VD_2$ undergo activation by their hydroxalation in the liver ($25OHVD_3$ and $25OHVD_2$) and are further metabolized by additional hydroxylation in the kidneys to $1,25(OH)_2VD_3$, $24,25(OH)_2VD_3$, $1,25(OH)_2VD_2$, and $24,25(OH)_2VD_2$.

Typically, measurement of Vitamin D in humans is performed by measurement of VD metabolites rather than the inactive VD prescursors. Metabolites $25OHVD_3$, $1,25(OH)_2VD_3$, $24,25(OH)_2VD_3$, $25OHVD$, $1,25(OH)_2VD_2$, and $24,25(OH)_2VD_2$ and other VD metabolites are generally referred to herein as "Vitamin D or VD."

Since Vitamin D levels in humans are directly affected by the function of the kidneys and liver, and since Vitamin D levels directly affect the regulation of calcium and phosphorous, the ability to measure Vitamin D in blood is important to the diagnosis and study of a broad range of diseases, including diseases of the bones, kidneys, and liver. Many other analytes in the broad category of secosteroids are similarly important for diagnostic purposes.

In the past, blood levels of secosteroids, including, for example, Vitamin D, have been determined from biological samples by methods including high-performance liquid chromatography, mass spectrometry, competitive protein binding assays, or other quantification techniques such as enzyme assays, immunoassays, chemical colorimetric assays, or fluorescence labeling. Methods known to the art further include methods of derivatizing analytes using Cookson-type reagents such as PTAD to generate a derivatized secosteroid or Vitamin D metabolites, purifying or extracting these analytes using liquid chromatography, and analyzing the purified sample for quantities or concentrations of the analytes using mass spectrometry. Current vitamin D analysis methods often lack the sensitivity and specificity required to address analytical problems pressing to the art, particularly attempts to discern the tissue distribution of the many forms of vitamin D. Commercially available kit assays known to the art allow high throughput analysis of 25(OH)D, but not of vitamin D, and inter-laboratory performance of these kits is poor. Kits known to the art generally utilize an extraction method from serum based on acetonitrile, followed by column separation to separate 25(OH)D from other metabolites. Kits using this method are unable to accurately and separately measure $25(OH)D_3$ and $25(OH)D_2$.

Also known to the art is the use of high-performance liquid chromatography (HPLC) coupled with mass spectrometry (LC-MS). This method offers increased sensitivity and selectivity over kits, particularly when Atmospheric pressure chemical ionization (APCI) is employed in combination with a Multiple Reaction Monitoring (MRM) technique. LC-MS techniques known to the art relying on APCI, however, also suffer several deficiencies. In particular, APCI often leads to the premature fragmentation of vitamin D molecules during ionization, decreasing the quality of and sensitivity of analysis and contributing to a higher variability with high LOQs.

Methods known to the art are further unable to establish satisfactory ionization efficiencies for the low (fmole) levels of some secosteroids analytes expected in biological matrices. Although attempts have been made to use electrospray ionization (ESI) in LC-MS to address this issue, the effectiveness of ESI is analyte-dependent and the structure of Vitamin D related molecules suggests they would not readily protonate during ESI, resulting in poor, if any, detection.

Methods of determining secosteroid levels in biological samples currently known to the art suffer a number of further disadvantages, including the length of time needed to complete the assay, level of accuracy, sensitivity, and cost. For instance, one approach for the extraction of Vitamin D and its isoforms common to the art is to deproteinize a sample solution suspected to contain Vitamin D, such deproteinization adapted to release Vitamin D metabolites that are bound to proteins within the sample solution. Such released Vitamin D may then be extracted using an organic solvent or derivatized using a Cookson-type reagent. Performing a liquid:liquid extraction and/or derivatization process of this kind typically is lengthy, and it requires a relatively large volume of available sample solution to generate a sufficient volume of extracted Vitamin D to analyze using chromatographic and/or MS separation and analysis techniques. Such traditional methods of performing assays are further labor intensive, requiring personnel to manually complete a series of preliminary tasks such as extraction, centrifugation, evaporation, and derivatization before the sample can be separated or purified, and, finally, analyzed for levels of the desired analytes. Further, derivatization with Cookson-type reagents is itself a comparatively lengthy process, routinely taking several hours to complete.

Accordingly, it is an object of versions of the present invention to provide a method of assaying biological samples for the levels, amounts, or concentrations of analytes, including specifically secosteroids, and most specifically Vitamin D, with improved accuracy and sensitivity, and without the need for lengthy and labor-intensive preparation steps prior to analysis. It is further an object of versions of the present invention to provide a method of assaying biological samples for Vitamin D with a reduced number of steps. These and other advantages are provided in the methods described below, and still further advantages to the methods claimed herein will be apparent to one skilled in the art.

SUMMARY

Versions of the present invention provide a method for detecting selected derivatized analytes in blood or other biological samples through mass spectrometry with a substantially reduced need for time and labor-intensive preparatory steps such as extraction, centrifugation, and evaporation. Versions of the present invention further provide an improved time of derivatization for analytes desired to be examined. Preferably, such analytes are secosteroids. Even more preferably, such analytes are metabolites of Vitamin D. Most preferably, steps of the method of the present invention are performed at least in part by use of a plasma separator device, or PSD.

A PSD according to versions of the present invention is a device that separates and aliquots a plasma sample of predetermined volume from a whole blood sample of sufficient size applied to the surface of the PSD. A PSD comprises a removable holding member, a blood introducing member in the holding member, a spreading layer member in communication with the blood introducing member, a semi-permeable separation member in communication with the spreading layer member, and a collection reservoir of defined volume in communication with the semi-permeable separation member, wherein when a whole blood sample is deposited on the blood introducing member, plasma from the sample passes through the spreading layer member to the separation member, is separated by the separation member, and is collected in a pre-determined volume by the collection reservoir. The collection reservoir may optionally further contain or comprise an absorptive material element, which absorbs substantially all of a collected plasma sample. The collection reservoir may be removed for convenient isolation of the collected plasma sample. The collected plasma sample may then be transferred to a preparation vessel for further processing, or, optionally, an absorptive material element that has substantially absorbed a collected plasma sample may be so transferred. A PSD may optionally be used for collection of other liquid or liquefied biological samples, including, for example, blood components, saliva, semen, cerebrospinal fluid, urine, tears and homogenized or extracted biosamples (i.e. from a whole organism, organ, tissue, hair, or bone).

Derivatizing agents according to the present invention are suitable compounds containing a positively charge group such as, preferably, a primary amine, selected to derivatize analytes including secosteroids and Vitamin D. Where Cookson-type derivatization agents known to the art contain a triazoline ring, derivitization agents according to the present invention contain one or more triazolidine rings. Derivatizing agents according to the present invention impart to the derivatized analyte a permanent positive charge, allowing more accurate and sensitive detection of the derivatized analyte by mass spectrometry. The derivatizing agent is a 4-substituted-1,2,4-triazolidine-3,5-dione or other functionally equivalent agent. Preferable derivatizing agents include 4-(1-methyl-4-pyrindinylmethyl)-1,2,4-triazolidine-3,5-dione, 4-phenyl-1,2,4-triazolidine-3,5-dione, and 4-ferrocenylmethyl-1,2,4-triazolidine-3,5-dione and their isomers, isotopes, and analogs.

Versions of the present invention include methods for determining the presence, concentration, or amount of analytes of interest in a biological fluid sample comprising the steps of collecting a biological fluid; separating liquid components from said biological fluid; aliquoting said liquid components; derivatizing analytes within said sample using a derivatizing agent; transferring said sample to a preparation vessel; fractionating said derivatized sample; and analyzing analytes of said sample.

Versions of the present invention further include methods of measuring the presence, amount, or concentration of analytes in a blood sample by the steps of collecting a whole blood sample; separating a plasma sample from said whole blood sample; collecting said plasma sample on a collection surface; allowing said plasma sample to dry on said collection surface; transferring said collection surface to a preparation vessel; adding a derivatizing agent to derivatize analytes suspected to be in the plasma sample; fractionating said derivatized sample; and analyzing said fractionated derivatized sample for the presence, amount, or concentration of analytes.

Preferably, the present invention includes methods for determining the presence, concentration, or amount of Vitamin D in a whole blood sample comprising the steps of collecting a whole blood sample; separating a plasma sample from said whole blood sample; aliquoting said plasma sample; derivatizing Vitamin D within said plasma sample using a derivatizing agent; transferring said sample to a preparation vessel; fractionating said sample; and analyzing Vitamin D within said sample. Most preferably, the method of versions of the present invention comprise the use of a PSD, which, when whole blood is introduced to the blood introducing area, separates and aliquots a plasma sample of predetermined volume into the collection reservoir. The collection reservoir of the PSD may optionally function as a collection surface for the plasma sample. Still further preferably, portions of a PSD, such as the blood holding member, semi-permeable member, collection reservoir, or absorptive material element may be treated with a derivatizing agent, which results in a collected plasma sample undergoing derivatization in the collection reservoir without any need to first remove said plasma sample from the collection reservoir. The collection reservoir may be placed in a collection reservoir, such as a tube or a glass vial for the extraction or derivatization. In these versions of the invention, separation, aliquoting, and the initiation of derivatization, although distinct operations, may occur virtually simultaneously.

Optionally, methods within the scope of the present invention can further comprise the addition of an internal standard to one or more plasma samples to permit greater precision in detecting the presence, amount, or concentration of analytes of interest using mass spectrometry. Preferably, internal standards comprise isotopically labeled coded versions of vitamin D and its isoforms, or isotopically labeled derivatizing agents used to form isotopically coded internal standards of derivatized analytes. Herein, "labeled" and "coded" shall be used interchangeably. Plasma samples, fluids, or liquefied samples can be treated with internal standards at any point prior to analysis. If the internal standard is an isotope of an analyte expected to be found in the plasma sample, the plasma sample is preferably treated with the internal standard prior to derivatization. Most preferably, in versions of the methods of the present invention in which a PSD is used, one or more of the blood holding area, semi-permeable membrane, collection reservoir, or absorptive material element of the PSD may be pre-loaded with an internal standard such that the plasma sample is treated with such internal standard as it is collected, separated, or aliquoted by the PSD. When a PSD is pre-loaded with an internal standard that is an isotopically labeled derivatizing agent, the plasma sample may undergo derivatization in the collection reservoir without any need to first remove said plasma sample from the collection reservoir. Also, the internal standard can be directly deposited on the collection reservoir before or after the collection of the plasma. In these versions of the invention, separation, aliquoting, application of an internal standard, and the initiation of derivitization, although distinct operations, can occur virtually simultaneously.

When a PSD is pre-loaded with an internal standard comprising an isotopically labeled analyte of interest, but is not pre-loaded with a derivatizing agent or an internal standard comprising a derivatizing agent, separation, aliquoting, and application of the internal standard, although sequentially distinct operations, may occur virtually simultaneously. It should be noted that portions of a PSD may be treated with one or more internal standards, with a derivatizing agent, or with one or more internal standards and a derivatizing agent, wherein such derivatizing agent may or may not itself comprise an internal standard.

Methods of the present invention may comprise the steps of collecting, separating, and aliquoting a plasma sample from a blood sample, treating the plasma sample with an internal standard, purifying the treated plasma sample, derivatizing the treated plasma sample, and analyzing the derivatized sample and internal standard mixture to compare the concentration or amount of the analytes in the sample with concentrations or amounts of internal standard to determine the concentration or amounts of analytes within the sample. Although the internal standard treatment step is described here as occurring after aliquoting, it will be appreciated by one skilled in the art that this step may, if the internal standard is a labeled analyte, occur at any point prior to derivatization, and, if the internal standard is a labeled derivatizing agent, will occur during derivatization. Similarly, as in all embodiments of the invention, although the derivatization step is listed as occurring after purification, it will be appreciated by one skilled in the art that it this step may occur at any point after separation of the plasma sample.

Preferably, one or more steps of these embodiments of the invention are accomplished by use of a PSD. Optionally, an internal standard can be pre-loaded in the blood holding member, semi-permeable member, collection reservoir, or absorptive material element of a PSD prior to collection of the plasma sample such that the plasma sample is treated with the internal standard through use of the PSD. Optionally, one or more of the sample, collection reservoir containing the sample, or absorptive material element containing the sample may be removed from the PSD and placed in a preparation vessel. The internal standard can then optionally be added to said preparation vessel.

Optionally, methods of the present invention may comprise the steps of collecting, separating, and aliquoting a multiple samples, treating each of these multiple samples with analytically distinct separate internal standards, purifying the treated samples, derivatizing the treated samples, and analyzing the derivatized samples as a batch to compare the concentration or amount of the analytes in the samples with concentrations or of amounts of internal standards to determine the concentration or amounts of analytes within the sample. Preferably, each sample is treated with a different internal standard, such differences preferably comprising differing isotopic labeling of the internal standards. Most preferably, internal standards in these versions of the invention comprise isotopically labeled derivatizing agents. Although the internal standard treatment step is described here as occurring after aliquoting, it will be appreciated by one skilled in the art that this step may, if the internal standard is a labeled analyte, occur at any point prior to derivatization, and, if the internal standard is a labeled derivatizing agent, will occur during derivatization. Similarly, as in all embodiments of the invention, although the derivatization step is listed as occurring after purification, it will be appreciated by one skilled in the art that it this step may occur at any point after separation of the plasma sample.

Preferably, one or more steps of these embodiments of the invention are accomplished by use of a PSD. Optionally, a derivatizing agent internal standard can be pre-loaded in the blood holding member, semi-permeable member, collection reservoir, or absorptive material element of a PSD prior to collection of the plasma sample such that the plasma sample is treated with the internal standard and derivatization is initiated through use of the PSD. The labeled compound is then analyzed using mass-spectrometry. The method can further comprise providing an internal standard comprising a known concentration of a known vitamin D derivatives, treating the known internal standard with derivatizing agents to form a derivatized standard adduct. The mixture of derivatized analyte and internal standard can be separated to form separated labeled analytes and internal standards, and the separated analytes and internal standards can be analyzed using mass spectrometry, using LC-MS, or LC-MSMS analysis of the derivatized adduct.

BRIEF DESCRIPTION OF THE DRAWINGS

FIG. 4 shows an exemplary comparison of the concentration of 25-hydroxy vitamin D3 (analyte) analyzed by versions of the present invention using a PSD and liquid-liquid extraction. D6-25-hydroxy vitamin D3 has been used as an internal standard.

FIG. 6 shows tables demonstrating reproducibility in peak area of analytes 25-hydroxy vitamin D2 (1, 2, 5, 10, and 20 pg) and 25-hydroxy vitamin D3 (2, 4, 10, 20, and 40 pg) shown in the linear regression analysis of FIG. 5 comparing with the peak area of the corresponding internal standards d6-25-hydroxy vitamin D2 (1, 2, 5, 10, and 20 pg) and d6-25hydroxy vitamin D3 (2, 4, 10, 20, and 40 pg), respectively.

DETAILED DESCRIPTION OF EMBODIMENTS OF THE INVENTION

Figure 1A:
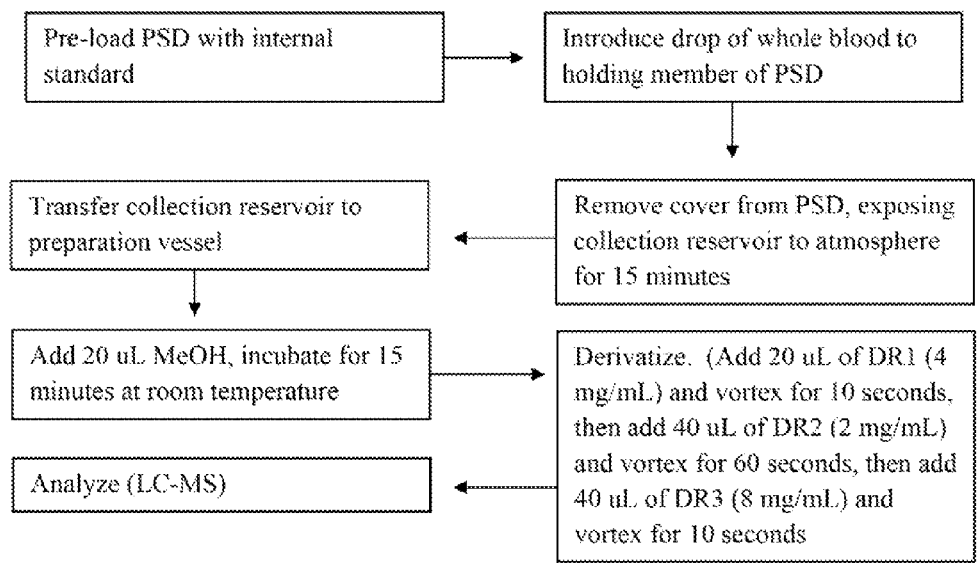
FIG. 1A is a block diagram of one embodiment of the method of the present invention, using a PSD.
Figure 1B:
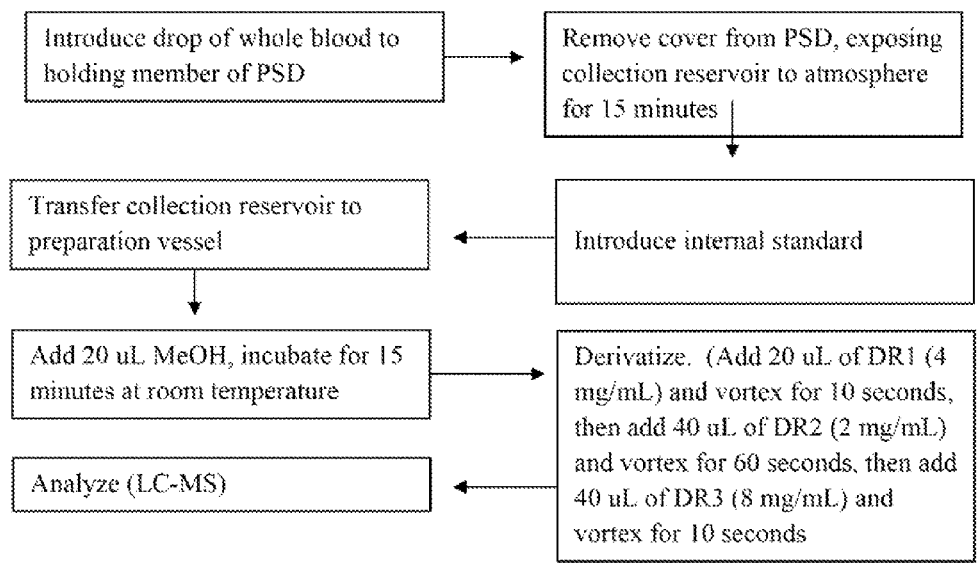
FIG. 1B is a block diagram of one embodiment of the method of the present invention, using a PSD.

While the composition and use of various versions of the present invention are discussed in detail below, it should be appreciated that the present invention includes a variety of particular embodiments that can be employed in a wide range of specific contexts. The specific versions and embodiments discussed herein are merely illustrative of the manners in which the present invention can be composed and used, and do not serve to limit the scope of the invention.

Specifically, as will be appreciated by one skilled in the art, various iterations and embodiments of the methods described below are presented, however, the invention is not limited to these iterations or embodiments, or to the specific order of steps presented herein. Variations in the number and order of steps, addition of other steps, and combinations of aspects of the various embodiments herein, all fall within the scope of the claimed invention. For example, and by way of illustration, although the embodiments disclosed herein discuss the derivatization step as occurring specifically before or after the separation or purification step, these steps can, as will be appreciated by one skilled in the art, be performed in various orders and at various times depending on the quality and character of the sample and the analytes of interest for analysis. The use of a PSD, as described a various points herein, can further result in the performance of one or more steps simultaneously or virtually simultaneously.

Terms used herein have meaning as commonly understood by one of ordinary skill in the relevant art, unless otherwise specifically defined herein While the terms herein are used to described particular embodiments and versions of the present invention, they are not intended to limit the scope of the invention except as specifically stated in the claims.

An "analyte" according to versions of the present invention refers to compounds or components desired to be measured in a sample. "Analytes" according to versions of the present invention can be any compound, component, or class of compounds that are or may be found in biological fluids, including specifically and preferably whole human blood or whole animal blood, that contain a diene reactive group. Preferably, analytes comprise secosteroids. Most preferably, analytes comprise Vitamin D and its metabolites, including Vitamin $D_2$, Vitamin $D_3$, 25OHD, 24,25$(OH)_2$D and 1,25$(OH)_2$D. "Analytes" further refers to isotopes, isomers, and analogs of all of the above. "Analytes of interest" refer to analytes for which a sample is to be analyzed, without regard to whether those analytes actually exist in the sample.

A "sample" according to versions of the present invention refers to any quantity of matter that is liquid or which has been liquefied, which is suspected of containing a quantity of one or more analyte of interest detectable by mass spectrometric analysis. Samples may include, by way of illustration, cells or cell cultures, organs, organ pieces or organ cultures, whole blood, plasma, serum, semen, hair, muscle, bone, saliva, tears, urine, feces, cerebrospinal fluid, or unknown substances suspected to contain detectable quantities of one or more analytes. Preferably, a sample refers to a quantity of whole blood, and, most preferably, of a quantity of human blood or its components such as plasma.

A "PSD" refers to a plasma separation device for use in various versions of the present invention. It will be appreciated that the PSD can separate, aliquot, and collect a plasma sample of pre-determined volume from a whole blood sample, saving time, labor, and effort compared to other methods of sample collection and preparation. Optionally, a PSD may, as described herein, be pre-loaded with a derivatizing agent, allowing the derivatization step to begin upon collection of the sample without the need for further action. Optionally, a PSD may, as described herein, be pre-loaded with an internal standard, allowing the step of treatment with an internal standard to begin upon collection of the sample without the need for further action.

A PSD may optionally be pre-loaded with a derivatizing agent by, prior to collection of a sample in the PSD, loading a desired quantity of derivatizing agent within the collection reservoir or, optionally, an absorptive material element of the PSD. It will be appreciated by one skilled in the art that the PSD may be pre-loaded with a derivatizing agent prior to use of the PSD, without respect to when the PSD is intended to be used to collect a sample. As will be appreciated by one skilled in the art, the effective shelf life of such a pre-loaded PSD will depend on the identity, stability, and rate of deterioration of the selected derivatizing agent.

A PSD may be optionally be pre-loaded with an internal standard by, prior to collection of a sample in the PSD, loading a desired quantity of internal standard within the collection reservoir, semi-permeable member, or, optionally, absorptive material element of the PSD. It will be appreciated by one skilled in the art that the PSD may be pre-loaded with an internal standard at any time prior to use, without respect to when the PSD is intended to be used to collect a sample. As will be appreciated by one skilled in the art, the effective shelf life of such a pre-loaded PSD will depend on the identity, stability, and rate of deterioration of the selected internal standard. Optionally, the blood holding member or semi-permeable member may be pre-loaded with an internal standard by treating or impregnating such members of the PSD with a desired amount of internal standard in liquid or solid form. Preferably, the internal standard is one or more of an isotopically labeled analyte of interest or an isotopically labeled derivatizing agent.

"Derivatizing" refers to the reaction of an analyte of interest with a derivatizing agent to create a new compound, referred to as a derivatized analyte, suitable for ionization and analysis through mass spectrometry. A "derivatizing agent" for the purpose of versions of this invention refers to suitable compounds containing a positively charged group such as, preferably a primary amine, selected to derivatize analytes including secosteroids and Vitamin D. Derivatizing agents according to the present invention contain one or more triazolidine rings. Derivatizing agents according to the present invention impart to the derivatized analyte a permanent positive charge, allowing more accurate and sensitive detection of the derviatized analyte by mass spectrometry. The derivatizing agent is a 4-substituted-1,2,4-triazolidine-3,5-dione or other functionally equivalent agent. Preferable derivatizing agents include 4-(1-methyl-4-pyrindinylmethyl)-1,2,4-triazolidine-3,5-dione, 4-phenyl-1,2,4-triazolidine-3,5-dione, and 4-ferrocenylmethyl-1,2,4-triazolidine-3,5-dione and their isomers, isotopes, and analogs.

It is believed that the use of a PSD incorporating an absorptive material element in preferred embodiments of the present invention assists with derivatization and purification through the following mechanism. Human blood contains approximately, on average, 100 ug/uL of protein. A 2.5 uL aliquot of plasma would, accordingly, contain on average approximately 250 ug of plasma protein. The absorptive material element has a volume potential of approximately 150% of the volume of the collection reservoir, or approximately 3.75 uL. The specific loading capacity of the absorptive material element is approximately 50 ug of protein per uL of volume potential of the element. Thus, a human whole blood sample separated through use of a PSD into an absorptive material element would yield approximately, on average, 187.5 ug of protein. Any Vitamin D analytes in the sample would be dispersed in this protein. When the liquid portion of the plasma sample is removed from the absorptive material element by evaporation, the remaining protein is believed to be deposited substantially in a monolayer, which can then be extracted by way, for example, an organic solvent. The believed monolayeric deposition of protein is believed to enhance the speed of extraction.

Preferably, the derivatizing agent is 4-(1-methyl-4-pyrindinylmethyl)-1,2,4-triazolidine-3,5-dione, or "DR1". DR1 can be synthesized as follows: 50 mmol of methyl hydrazinocarboxylate (Sigma, FW 90.08) is dissolved in 50 ml of anhydrous THF under $N_2$. Fifty mmol of 1,1'-carbonyldiimidazole (Sigma, FW 162.15) is added in portions over a two to three minute period. The mixture is stirred at room temperature for 15 minutes. Fifty mmol of 4-aminomethylpyridine (Sigma, FW 108.14) is added and the mixture is stirred at room temperature overnight. The solid product ("Compound I") is collected by filtration and washed with THF. Twenty mmol of Compound 1 is refluxed in 10 ml of 4 M KOH for 2 hours, then is allowed to cool to room temperature. The mixture is then stirred in an ice water bath, and, while so cooled, is titrated with concentrated HCl until the appearance of bulk precipitate, which occurs after consumption of approximately 4 ml HCl and at a pH of approximately 6. The solid product (Compound II) is collected by filtration, washed with water, and dried. Five mmol of Compound II is added to 15 volumes of acetone. A total amount of 5 times excess of iodomethane (Sigma, FW 141.94) is added to the solid. The solid is placed in a vessel and sealed, then placed in an oven at 50° C. oven for 6 days. The dried solid product substantially comprises DR1. Many of the examples of versions of the present invention also utilize an oxidizing agent and a stabilizing agent, as will be appreciated by one skilled in the art. Preferably, the oxidizing agent is preferably iodobenzene diacetate, referred to herein as "DR2", and the stabilizing agent (or "stabilizer" is ascorbic acid, referred to herein as "DR3".

An "internal standard" refers to a substance added in a known amount prior to analysis of a sample, wherein a mass spectrometric signal of the known internal standard can be compared to the mass spectrometric signal, if any, of analytes of interest within the sample, and, through this comparison, the presence and amount of analytes of interest can be determined. An ideal internal standard is a substance with a highly similar, and, if possible, identical chemical structure to the analyte of interest, that differs only by the presence of "heavy" atoms at specific sites in the standard. For instance, a deuterium isotope of VD, in which a deuterium atom is substitute for a hydrogen atom, is an appropriate internal standard for VD. Although the analyte and internal standard differ in mass and are recognized individually by mass spectrometry, their fragmentation patterns and relative yields of fragment ions are substantially identical. Internal standards preferably comprise one or more isotopically labeled analytes of interest, or one or more isotopically labeled derivatizing agents.

Internal standards that comprise isotopically labeled analytes of interest preferably comprise isotopically labeled sec-osteriod compounds, and most preferably comprise isotopically labeled metabolites of Vitamin D. Internal standards that comprise isotopically labeled derivatizing agents preferably comprise isotopes of DR1.

"Isotopic labeling," "isotopically labeled," "coding," or "coded" refers to the replacement of one or more atoms within an internal standard molecule with an atom containing the same number of protons and electrons, but varying numbers of neutrons. Isotopic labels produce a mass shift in the isotopically labeled molecule relative to the unlabeled molecule when analyzed by mass spectrometric techniques, wherein the amount of the unlabeled molecule can be determined by comparison of its mass spectrometric signature with the mass spectrometric signature of the labeled internal standard molecule. Since the gas phase fragmentation pattern produced during mass spectrometery is independent of isotope labeling, use of isotopically labeled internal standards is appropriate for methods of the present invention. Suitable isotopic labels include, by way of example, deuterium ($^2H$), $^{13}C$, and $^{15}N$. For example, a 25-hydroxy vitamin D3 molecule isotopically labeled with deuterium would be 3 atomic mass units (amu) greater than an unlabeled 25-hydroxy vitamin D3 molecule, resulting in a detectable mass shift differentiating the 25-hydroxy VD3 molecule and its isotopically labeled internal standard when both are analyzed through MS. An isotopic label can be incorporated at one or more positions in a molecule, and one or more isotopic labels can be used on the same isotopically labeled molecule.

"Purifying" a sample according to versions of the present invention refers to least partially separating analytes of interest, if any, from the remaining components of a sample without substantially altering the properties of the analyte of interest. Purification or purifying does not refer to removing all materials from the sample other than analytes of interest, rather, it refers to a procedure that enriches the amount of analytes of interest, if any, relative to other components in the sample that might interfere with mass spectrometric analysis of the analytes of interest. Purification allows relative reduction within the sample of one or more substances that may interfere with the detection of analytes of interest by mass spectrometry. This relative reduction does not require that any substance present in the sample be substantially or entirely removed. A sample is at least partially separated from other substances within the scope of versions of the present invention once such relative reduction has occurred.

Purification can be achieved by any suitable means. As will be apparent to one skilled in the art, purification can be accomplished by means including, for example, precipitation, titration, filtration, capillary electrophoresis, gas chromatography, fractionation, ion mobility separation, electrospray ionization (ESI), matrix assisted laser desorption ionization (MALDI), direct electrospray ionization (DESI), solvent extraction, centrifugation, or dilution. Preferably, purification in versions of the present invention refers to liquid chromatography ("LC"), including high-performance liquid chromatography ("HPLC").

As used herein "chromatography" generally refers to a process in which a chemical mixture carried by a liquid or gas is separated into components as a result of differential distribution of the chemical entities as they flow around or over a stationary liquid or solid phase. LC refers to a process of selective retardation of one or more components of a fluid solution as the fluid uniformly percolates through a column of finely divided substance, or through capillary passageways. The retardation results from the distribution of the components of the mixture between one or more stationary phases and the bulk fluid (or mobile phase), as this bulk fluid moves relative to the stationary phases. Examples of LC include reverse phase liquid chromatography, high performance liquid chromatography, turbulent flow liquid chromatography, and high throughput liquid chromatography.

As used herein, "gas chromatography" or GC refers to chromatography in which the sample mixture is vaporized and injected into a stream of carrier case, such as nitrogen or helium, which stream moves through a column containing a stationary phase composed of a liquid or particulate solid. The sample mixture is separated according to the affinity of the compounds within the sample mixture for the stationary phase.

"Analyzing" refers to employing appropriate techniques to determine the presence or absence and, optionally, amount or concentration, of one or more analytes of interest. Specifically, analyzing refers to employing quantitative analytical techniques to measure the presence, amount, or concentration of one or more derivatized analytes of interest, at least in part by taking advantage of the positive charge imparted to the derivatized analyte by the derivatizing agent. Analysis preferably refers to techniques of mass spectrometry, including single-dimension mass spectrometry and tandem mass spectrometry. The derivatized compound is then analyzed using mass-spectrometry. The method can further comprise providing a internal standard comprising a known concentration of a vitamin D, vitamin D derivatives or vitamin D having deuterium, treating the known internal standard with the derivatizing reagent to form a derivatized standard adduct. The mixture of derivatized analyte and internal standard can be separated to form a separated peak with differential mass or/and retention time in a chromatography, and the separated analytes and internal standards can be analyzed using mass spectrometry, using LC-MS or LC-MSMS analysis of the derivatized adduct.

"Mass spectrometry" or "MS" refers to a method for analysis of compounds by their mass. MS includes methods of filtering, detecting, and measuring ions based on their mass-to-charge ration ("m/z"). As will be appreciated by one skilled in the art, MS generally includes: (1) ionizing a compound to be analyzed to form charged compounds; (2) detecting the molecular weight of the charged compounds; and (3) calculating a mass-to-charge ratio for the detected charged compounds. Ionization may occur by any suitable means, as will be apparent to one skilled in the art. Suitable means of ionization include, by way of illustration, atmospheric pressure chemical ionization, atmospheric pressure photoionization, inductively coupled plasma, field desorption, laser diode thermal desorption, electrospray ionization, fast atom bombardment, matrix-assisted laser desorption ionization ("MALDI"), or surface-enhanced laser desorption ("SELDI"). Ion detection may also be performed by any suitable means, as will be apparent to one skilled in the art. By way of example, detection may be performed in positive ion mode, or, alternatively, negative ion mode. Detection may if desired be performed using selective ion monitoring or multiple reaction mode ("MRM"). In some embodiments, parent daughter ion transition monitoring (PDITM), selective reaction monitoring (SRM), or MRM of derivatized analytes is performed using a triple quadrupole MS platform.

The "lower limit of quantification" refers to the point where MS measurements become quantitatively meaningful. It is the lowest point at which analyte response is identifiable, discrete, and reproducible with a relative standard deviation of less than 20% and accuracy of greater than 80%. The "limit of detection" refers to the point at which the value measured using mass spectrometry is equal to or less than the uncertainty associated with that value, and is defined as three times the relative standard deviation of the mean at zero concentration.

Preferred versions of the present invention include a method for determining the presence or amount of analytes of interest in a plasma sample comprising the steps of collecting a blood sample; separating a plasma sample from said blood sample; aliquoting said plasma sample; derivatizing analytes of interest within said plasma sample using a derivatizing agent; transferring said sample to a preparation vessel; purifying said sample; and analyzing the presence, absence, amount, or concentration of analytes of interest. It should be appreciated that multiple steps of this method may be performed virtually simultaneously, such as when a PSD is employed. Further, it will be appreciated that some steps may, depending on the laboratory techniques used, be omitted or performed in varying orders. By way of illustration, derivatization may occur after purification, and the step of transferring the sample to a preparation vessel may in some circumstances be omitted as described herein.

Preferably, collection of the plasma sample is accomplished by use of a PSD. A PSD may perform the steps of collecting a whole blood sample, separating a plasma sample from the whole blood sample, and aliquoting the plasma sample to a known volume, virtually simultaneously. A PSD may also be pre-loaded with one or more internal standards or one or more derivatizing agents in the blood holding member, semi-permeable member, collection member, or absorptive material element.

Prior to analysis, a plasma sample may be treated with one or more separately detectable internal standards. Optionally, an internal standard may be added prior to or during deriviti-zation. Preferably, the derivatizing agent may also comprise an internal standard.

Figure 2:
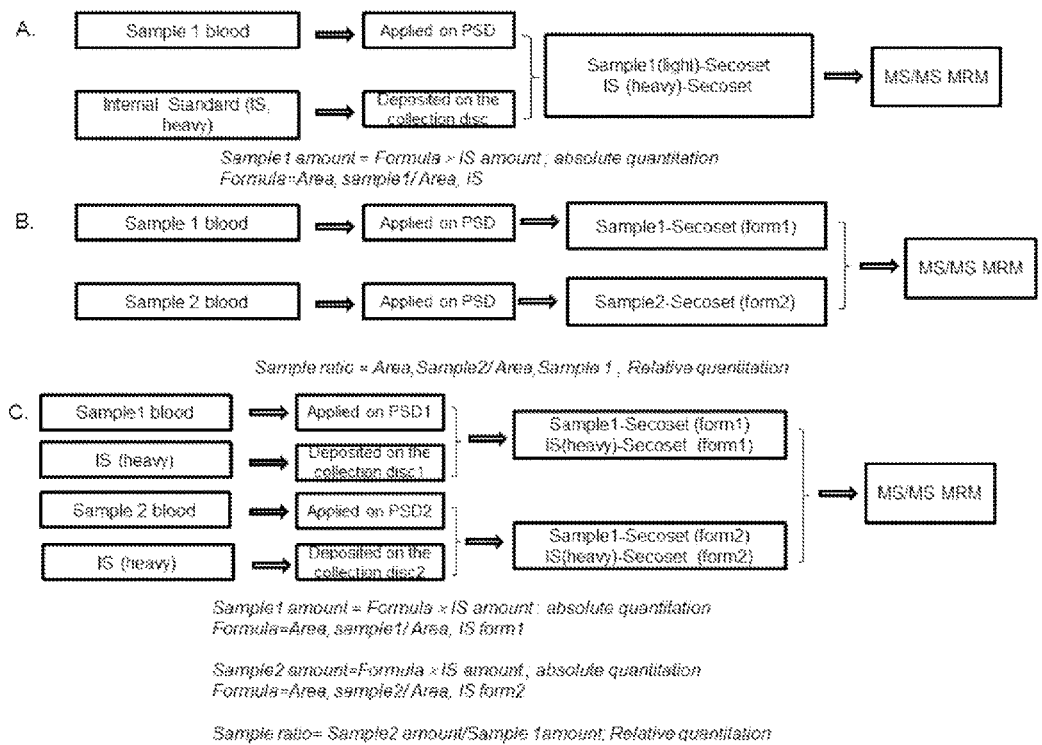
FIG. 2 is a flow chart depicting various strategies for analysis within the scope of the embodiments of the present invention using internal standards to evaluate analytes in multiple samples.

Optionally, two or more plasma samples may be mixed prior to analysis and analyzed in a batch. Preferably, when analyzing two or more plasma samples in a batch, at least one of said plasma samples is treated with an internal standard prior to mixing the plasma samples. Preferably, each plasma sample to be mixed is, prior to mixing, treated with an internal standard distinct from the internal standards used to treat the other plasma samples to be mixed as part of the batch. Such internal standards can comprise different isotopes of one or more analyte of interest, different isotopes of the derivatizing agent or agents, or a combination of one or more isotopes of an analyte of interest and one or more isotopes of a derivatizing agent. FIGS. 2, 2A, and 2B, for example, illustrate the absolute and relative quantitation of an assay incorporating two plasma samples treated with distinct internal standards. As shown in FIG. 2A, analyte of interest Vitamin D in two plasma samples may be collected, aliquoted, and extracted through the use of a separate PSD for each sample. Each sample is treated with a distinct internal standard, such as a 1-deuterium isotope of Vitamin D, and the samples are mixed. The mixed samples are then derivatized DR1. Subsequently, the mixture can be subjected to separation, for example, on a reversed phase column. The labeled analytes and internal standards can elute from the column at separate times due to their different and distinct retention time on the column. The peaks eluted from the reversed phase column comprise peaks that include the derivatized analytes from unknown sample and peaks that include the derivatized internal standards or analytes having known concentration or amount.

In versions of the invention that use a PSD, optionally the plasma sample can be derivatized after the sample is collected in the collection reservoir of the PSD by placing the collection reservoir of the PSD into a solution comprising in part a derivatizing agent without first removing the sample from the collection disc. Optionally, the collection reservoir may be removed from the PSD and placed in a preparation vessel to which a derivatizing agent may then be added. Preferably, the collection reservoir is an absorptive material element. In these preferred embodiments, the absorptive material element may be placed directly in a preparation vessel with a solvent, to which a derivatizing agent may also be added.

In another embodiment of the invention, the method comprises the steps of collecting a whole blood sample; separating a plasma sample from said whole blood sample; aliquoting said plasma sample; derivatizing analytes within said plasma sample using a derivatizing agent; transferring said sample to a preparation vessel; purifying said sample; and analyzing analytes of interest, if any, within said sample.

In another embodiment of the present invention the method comprises the steps of collecting a whole blood sample; separating a plasma sample from said whole blood sample; collecting said plasma sample on a collection surface; allowing said plasma sample to dry on said collection surface; derivatizing analytes within said plasma sample by adding a derivatizing agent to the collection surface; transferring said collection surface to a preparation vessel; purifying said sample from said collection surface and other components; and analyzing analytes of interest, if any, within said sample.

In another embodiment of the present invention the method comprises the steps of collecting a whole blood sample; separating a plasma sample from said whole blood sample; collecting said plasma sample in an absorptive material element; allowing said plasma sample to dry in said absorptive material element; placing derivatizing analytes within said plasma sample by adding a derivatizing agent to said absorptive material element; transferring said absorptive material element to a preparation vessel; purifying said sample from said absorptive material element and other components; and analyzing analytes of interest, if any, within said sample.

Methods of the present invention optionally comprise collecting, separating, and aliquoting a plasma sample, treating the plasma sample with an internal standard, purifying the plasma sample, derivatizing the plasma sample, and analyzing the sample and internal standard mixture to compare the concentration or amount of analytes of interest, if any, in the sample with concentrations or of amounts of internal standard, to determine the presence, amount, or concentration of analytes of interest. Although the internal standard treatment step is described here as occurring after aliquoting, it will be appreciated by one skilled in the art that this step may, if the internal standard is a labeled analyte, occur at any point prior to derivatization, and, if the internal standard is a labeled derivatizing agent, will occur during derivatization. Preferably, one or more steps of methods of this embodiment of the invention can be accomplished by use of a PSD. Optionally, the internal standard can be pre-loaded in the blood holding member, semi-permeable member, collection reservoir, or absorptive material element of a PSD prior to collection of the plasma sample.

Optionally, methods of the present invention may comprise the steps of collecting, separating, and aliquoting a multiple plasma samples, treating each of these multiple plasma samples with separate internal standards, purifying the samples, derivatizing the samples, mixing the samples, and analyzing the derivatized mixed samples as a batch to determine the presence, concentrations, or amounts of analytes of interest within each sample. Preferably, each plasma sample is treated with a different internal standard prior to mixing, such differences preferably comprising differing isotopic labeling of the internal standards. Although the internal standard treatment step is described here as occurring after aliquoting, it will be appreciated by one skilled in the art that this step may, if the internal standard is a labeled analyte, occur at any point prior to derivatization, and, if the internal standard is a labeled derivatizing agent, will occur during derivatization and may occur at any point prior to mixing the samples to be analyzed as a batch. Preferably, one or more steps of methods of this embodiment of the invention can be accomplished by use of a separate PSD for each sample. Optionally, each separate PSD can be pre-loaded with an analytically distinct internal standard in its blood holding member, semi-permeable member, collection reservoir, or absorptive material element.

EXAMPLES

Example 1

In a version of the invention in which analytes of interest Vitamin D2 and D3 are sought in a sample of whole human blood, a human whole blood sample with a volume of approximately 25 uL is introduced to a PSD. After 3 minutes, the collection reservoir containing a 2.4 uL aliquoted plasma sample is removed from the PSD is allowed to air dry for an additional 15 minutes. Plasma is separated from said whole blood sample by the semi-permeable membrane of said PSD. The reservoir is placed into a preparation vessel constituting a 2 mL polypropylene tube and is treated with 2 μL of the internal standard d6-25OHVD2 (10 pg/uL) and d6-25OHVD3 (20 pg/uL) in MeOH. The reservoir is allowed to dry for an additional 3 minutes. The disc is incubated for 15 minutes at room temperature. Twenty uL of DR1 (4 mg/mL in MeOH) is added to the reservoir. The reservoir is vortexed for 10 seconds. Forty uL of DR2 is then added (2 mg/mL in MeOH) and the reservoir is vortexed for an additional 60 seconds.

Figure 3:
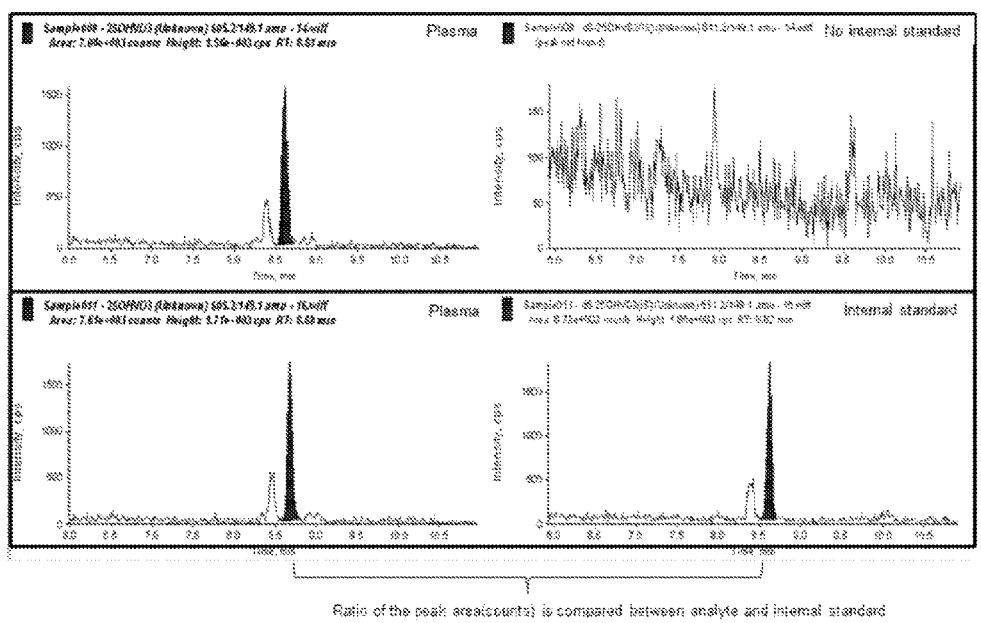
FIG. 3 shows a mass spectrometric readout using Multiple Reaction Monitoring of the analyte of interest 25-hydroxy vitamin D3 in plasma, treated with D6-25-hydroxyl vitamin D3 as an internal standard, through use of a PSD, as described in example A of FIG. 2.
Figure 5:
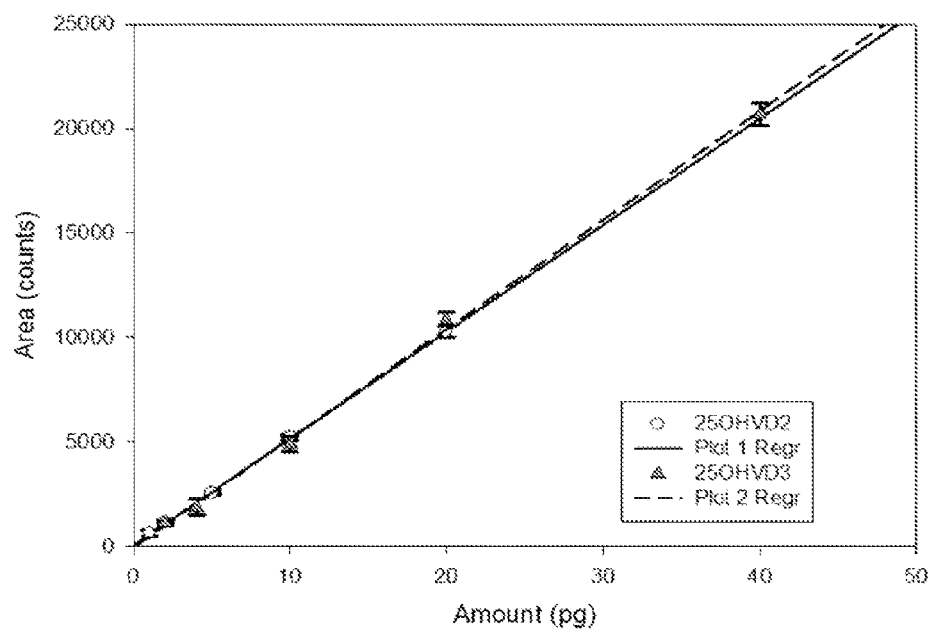
FIG. 5 shows a linear regression analysis for the comparison of mass spectrometric determinations of standard 25-hydroxy vitamin D2 against 25-hydroxy vitamin D3 with derivatization and using a PSD according to embodiments of the present invention.
Figure 7:
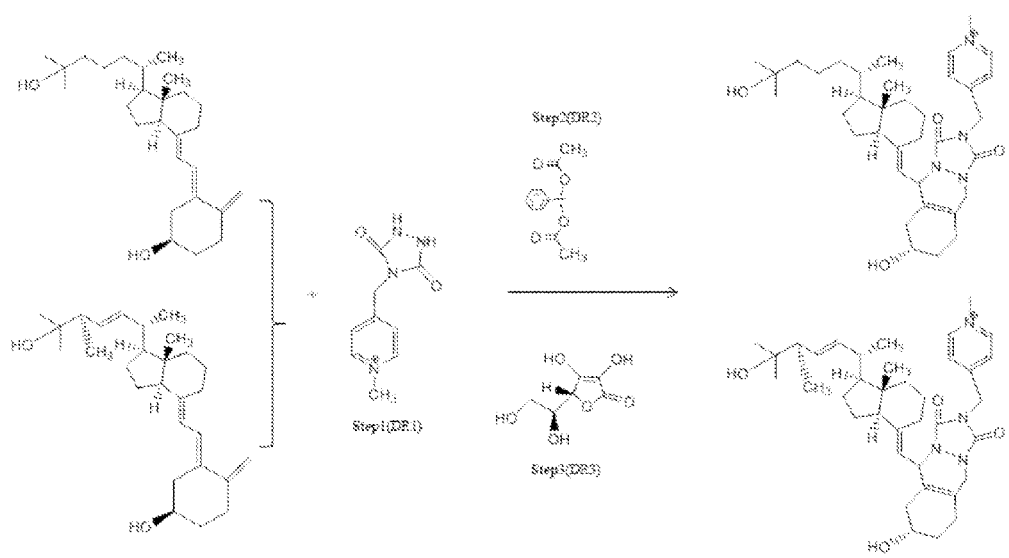
FIG. 7 shows the derivatization mechanism of a 25-hydroxy vitamin D3 and 25-hydroxy vitamin D2 with 4-(1-methyl-4-pyrindinylmethyl)-1,2,4-triazolidine-3,5-dione.
Figure 8:
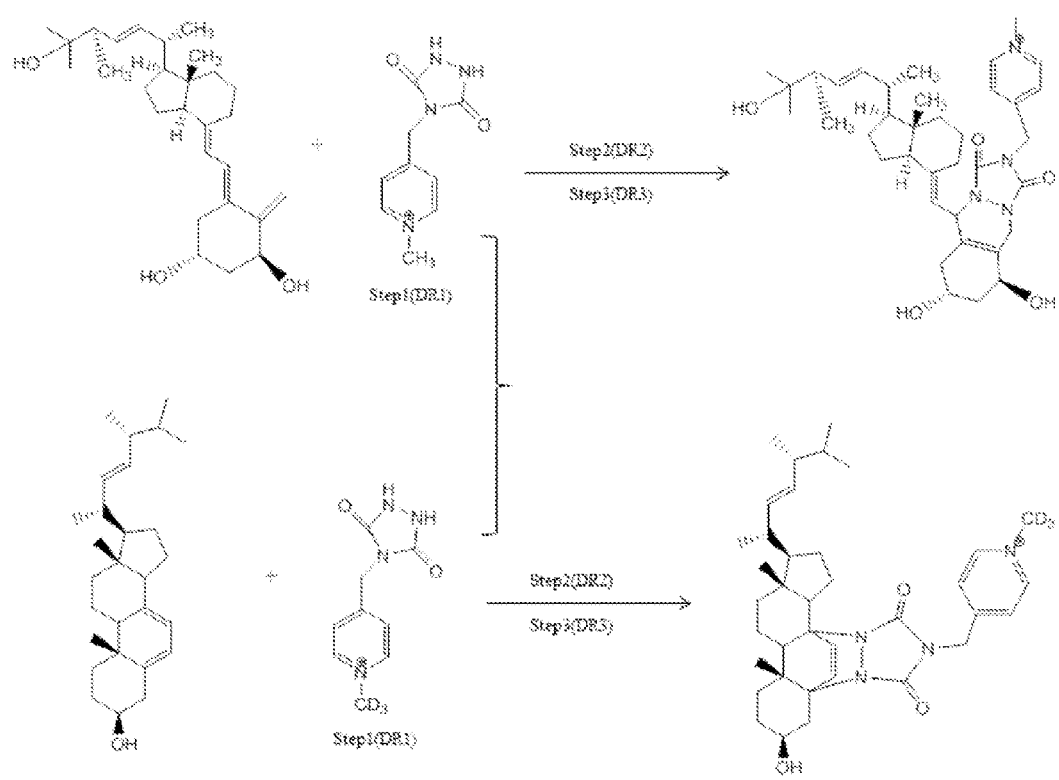
FIG. 8 shows the derivatization of 1α, 25-dihydroxy vitamin D2 with 4-(1-methyl-4-pyrindinylmethyl)-1,2,4-triazolidine-3,5-dione and ergosterol with 4-(1-(methyl-D3)-4-pyrindinylmethyl)-1,2,4-triazolidine-3,5-dione, respectively, in embodiments of the present invention.

The derivatization reaction is quenched by adding 40 uL of DR3 (8 mg/mL in H2O). The solution is then vortexed for 10 seconds. The sample is transferred, without any solid remaining portions of the reservoir, to a new vial. The sample is then analyzed by LC/MS. Fifteen uL of the sample is injected into a reverse phase column, separated by LC, and analyzed by MS. As shown in the FIG. 3, the absolute concentrations of VD2 and VD3 are determined by comparing the peak areas of the analytes of interest with the known peak areas of the internal standards.

Suggested LC-MS/MS conditions include:

Temperature at autosampler was set to 4° C., Temperature at oven was set to 40° C.

Solvent A: 100% $H_2O$/0.05% formic acid, and

Solvent B: 100% ACN/0.05% formic acid can be used.

C18 column (250×2.1 mm) HALO; gradient from 35% water (0.05% formic acid) to 50% acetonitrile (0.05% formic acid); flow rate of 0.2 mL/min

| Time(min) | % B |
|---|---|
| 4 | 35 |
| 14 | 50 |
| 15 | 100 |
| 18 | 100 |
| 18.1 | 25 |
| 21 | stop |

QTRAP4000 triple quadrupole-linear ion trap mass analyzer (AB Sciex) was used in ESI-positive ion mode. Unit resolution was used.

| | | Retention time(min)* | MRM transitions | CE | CXP (volts) | DP | EP |
|---|---|---|---|---|---|---|---|
| 25OHVD2 | L | (10.26/9.81) | 617.4/149.1 | 89 | 6 | 85 | 10 |
| d6-25OHVD2 | H | (10.20/9.76) | 623.4/149.1 | 89 | 12 | 85 | 10 |
| 25VD3 | L | (9.50/9.25) | 605.4/149.1 | 93 | 12 | 85 | 10 |
| d6-25OHVD2 | H | (9.44/9.18) | 611.4/149.1 | 85 | 6 | 85 | 10 |

Suggested Reference Source Parameters

Curtain gas: 20

Collision gas: high

Ion spray voltage: 5000

Temp: 450

Ion source gas 1: 30

Ion source gas 2: 50

|  | Q1 | Q3 |  | Q1 | Q3 |
|---|---|---|---|---|---|
| 25OHVD3 | 605.4 | 149.1 | d6-25OHVD3 | 611.4 | 149.1 |
| 25OHVD2 | 617.4 | 149.1 | d6-25OHVD2 | 623.4 | 149.1 |
| 1,25OHVD3 | 621.4 | 149.1 | d6-1,25OHVD3 | 627.4 | 149.1 |
| 1,25OHVD2 | 633.4 | 149.1 | d6-1,25OHVD2 | 639.4 | 149.1 |

Example 2

Figure 9:
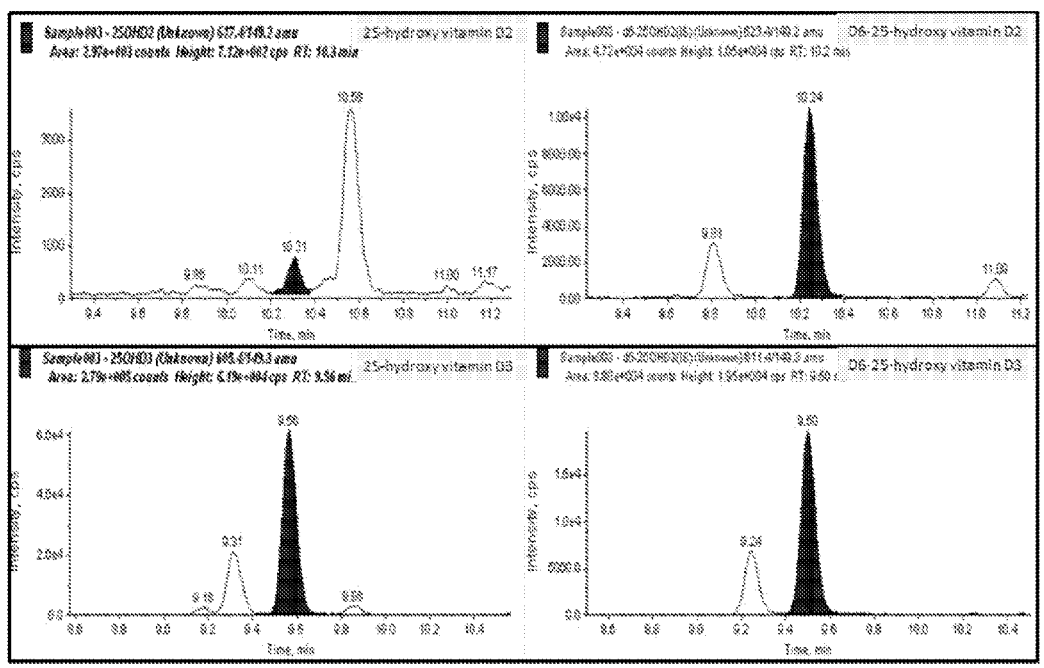
FIG. 9 shows a mass spectrometric readout using Multiple Reaction Monitoring of the analytes of interest 25-hydroxy vitamin D2 and 25-hydroxy vitamin D3 in plasma, treated with D6-25-hydroxyl vitamin D2, and D6-25-hydroxyl vitamin D3 as an internal standards, through the liquid-liquid extraction detailed in Example 2.

Venously drawn blood was separated into plasma by using centrifugation. Fifty or 100 uL of the plasma is placed into a tube and 50 uL of internal standard is added. After adding 50 uL of phosphate buffer, the mixture is vortexed and then allowed to equilibrate under dark for 1-2 hours at room temperature. One mL of MTBE (methyl t-butyl ether) is added and liquid-liquid extraction (LLE) is performed. Following 2 minutes of vortexing, samples are centrifuged for 10 minutes. The samples are stored at least for 30 minutes at a temperature of −80 degrees C. The liquid upper layer is poured into a vessel and dried at 30° C. with nitrogen gas. The vessel is vortexed for 10 seconds with addition of fifty uL of DR1 (2 mg/mL in MeOH). Fifty uL of DR2 is added (2 mg/mL in MeOH) and the vessel is vortexed for an additional 60 seconds. The derivatization reaction is quenched by adding 50 uL of DR3 (8 mg/mL in H2O). The solution is then vortexed for 10 seconds. The sample is transferred, without any solid remaining portions, to a new vessel. The sample is then analyzed by LC/MS. Fifteen uL of the sample is injected into a reverse phase column, separated by LC, and analyzed by MS. As shown in FIG. 9, the absolute concentrations of VD2 and VD3 are determined by comparing the peak areas of the analytes of interest with the known peak areas of the internal standards.

Thus, specific compositions and methods of determining analytes of interest from a sample have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method for determining the presence, concentration, or amount of analytes of interest in a sample comprising the steps of:
   a. collecting a biological fluid;
   b. separating a liquid sample from said biological fluid;
   c. aliquoting said sample;
   d. derivatizing analytes of interest within said sample, wherein the derivatizing agent comprises at least one of: 4-(1-methyl-4-pyridinylmethyl)-1,2,4-triazolidine-3,5-dione, 4-phenyl-1,2,4-triazolidine-3,5-dione, and 4-ferrocenylmethyl-1,2,4-triazolidine-3,5-dione, and their isomers, isotopes, and analogs;
   e. transferring said sample to a preparation vessel;
   f. purifying said sample; and
   g. analyzing analytes of interest of said sample.

2. The method of claim 1 in which said a biological fluid is whole blood.

3. The method of claim 1 in which said liquid sample is separated and aliquoted by use of a PSD.

4. The method of claim 3 in which at least one of the blood holding member, semi-permeable member, and collection reservoir of said PSD is pre-loaded with at least one of a derivatizing agent and at least one internal standards.

5. The method of claim 4 in which at least one of the blood holding member, semi-permeable member, and collection reservoir of said PSD is pre-loaded with a derivatizing agent.

6. The method of claim 5 in which at least one derivatizing agent is isotopically tagged.

7. The method of claim 1 in which said liquid sample is purified by at least one of liquid chromatography, mass spectrometry, capillary electrophoresis, gas chromatography, solvent extraction, filtration, precipitation, centrifugation, and dilution.

8. The method of claim 1 in which said liquid sample is analyzed by mass spectrometry.

9. The method of claim 1 further comprising the step, prior to analysis, of treating said sample with an internal standard.

10. The method of claim 9 in which said internal standard comprises at least one of an isotopically labeled analyte of interest and an isotopically labeled derivatizing agent.

11. The method of claim 10 in which said liquid sample is separated and aliquoted by use of a PSD and said internal standard is loaded in at least of the sample holding member, semi-permeable member, and collection reservoir of said PSD prior to introduction of said sample.

12. A method for determining the presence, concentration, or amount of secosteroids of interest in a blood sample comprising the steps of:
   a. collecting whole blood;
   b. separating a plasma sample from said whole blood sample;
   c. aliquoting said plasma sample;
   d. derivatizing secosteroids within said plasma sample using a derivatizing agent, wherein the derivatizing agent comprises at least one of: 4-(1-methyl-4-pyrindinylmethyl)-1,2,4-triazolidine-3,5-dione, 4-phenyl-1,2,4-triazolidine-3,5-diaone, and 4-ferrocenylmethyl-1,2,4-triazolidine-3,5-dione, and their isomers, isotopes, and analogs,
   e. transferring said sample to a preparation vessel;
   f. purifying said sample; and
   g. analyzing desired components of said sample.

13. The method of claim 12 in which said plasma sample is separated and aliquoted by use of a PSD.

14. The method of claim 13 in which at least one of the blood holding member, semi-permeable member, and collection reservoir of said PSD is pre-loaded with at least one of a derivatizing agent and at least one internal standards.

15. The method of claim 14 in which at least one derivatizing agent is isotopically tagged.

16. The method of claim 12 in which said sample is purified by at least one of liquid chromatography, mass spectrometry, capillary electrophoresis, gas chromatography, solvent extraction, filtration, precipitation, centrifugation, and dilution.

17. The method of claim 12 in which said sample is analyzed by mass spectrometry.

18. The method of claim 12 further comprising the step, prior to analysis, of treating said sample with an internal standard.

19. The method of claim 18 in which said internal standard comprises at least one of an isotopically labeled analyte of interest and an isotopically labeled derivatizing agent.

20. The method of claim 19 in which said sample is separated and aliquoted by use of a PSD and said internal standard is loaded in at least one of the sample holding member, semi-permeable member, and collection reservoir of said PSD prior to introduction of said sample.

21. The method of claim 18 in which:
    (a) multiple plasma samples are separately treated with multiple internal standards, wherein each of said internal standards is analytically distinct from each other of said internal standards; and
    (b) after each said sample is treated with one of said internal standards, said samples are analyzed as a batch.

22. The method of claim 21 in which each of said samples is separated and aliquoted by use of a separate PSD and each PSD is loaded with an analytically distinct internal standard in at least one of the sample holding member, semi-permeable member, and collection reservoir of said PSD prior to introduction of said sample.

23. A method for determining the presence, concentration, or amount of Vitamin D in a blood sample comprising the steps of:
    a. collecting whole blood;
    b. separating a plasma sample from said whole blood sample;
    c. aliquoting said plasma sample;
    d. derivatizing Vitamin D within said plasma sample using a derivatizing agent, wherein the derivatizing agent comprises at least one of: 4-(1-methyl-4-pyrindinylmethyl)-1,2,4-triazolidine-3,5-dione, 4-phenyl-1,2,4-triazolidine-3,5-dione, and 4-ferrocenylmethyl-1,2,4-triazolidine-3,5-dione, and their isomers, isotopes, and analogs,
    e. transferring said sample to a preparation vessel;
    f. purifying said sample; and
    g. analyzing desired components of said sample.

24. The method of claim 23 in which said plasma sample is separated from said whole blood sample and aliquoted by use of a PSD.

25. The method of claim 24 in which at least one of the blood holding member, semi-permeable member, and collection reservoir of said PSD is pre-loaded with at least one of a derivatizing agent and at least one internal standards.

26. The method of claim 25 in which at least one derivatizing agent is isotopically tagged.

27. The method of claim 23 in which said sample is purified by at least one of liquid chromatography, mass spectrometry, capillary electrophoresis, gas chromatography, solvent extraction, filtration, precipitation, centrifugation, and dilution.

28. The method of claim 23 in which said sample is analyzed by mass spectrometry.

29. The method of claim 23 further comprising the step, prior to analysis, of treating said sample with an internal standard.

30. The method of claim 29 in which said internal standard comprises at least one of an isotopically labeled analyte of interest and an isotopically labeled derivatizing agent.

31. The method of claim 30 in which said sample is separated and aliquoted by use of a PSD and said internal standard is loaded in at least one of the sample holding member, semi-permeable member, and collection reservoir of said PSD prior to introduction of said sample.

32. The method of claim 29 in which:
    (a) multiple plasma samples are separately treated with multiple internal standards, wherein each of said internal standards is analytically distinct from each other of said internal standards; and
    (b) after each said sample is treated with one of said internal standards, said samples are analyzed as a batch.

33. The method of claim 32 in which each of said samples is separated and aliquoted by use of a separate PSD and each PSD is loaded with an analytically distinct internal standard in at least one of the sample holding member, semi-permeable member, and collection reservoir of said PSD prior to introduction of said sample.

34. A method for determining the presence, concentration, or amount of analytes of interest in a plasma sample comprising the steps of:
    a. Collecting, separating, and aliquoting a plasma sample by use of a PSD, wherein said collection reservoir of said PSD comprises an absorptive material element and said aliquoted plasma sample becomes substantially absorbed by said absorptive material element;
    b. Preparing said plasma sample for analysis by derivatizing said sample, wherein the derivatizing agent comprises at least one of: 4-(1-methyl-4-pyrindinylmethyl)-1,2,4-triazolidine-3,5-dione, 4-phenyl-1,2,4-triazolidine-3,5-dione, and 4-ferrocenylmethyl-1,2,4-triazolidine-3,5-dione, and their isomers, isotopes, and analogs;
    c. Purifying said plasma sample; and
    d. Analyzing said plasma sample.

35. The method of claim 34, wherein the preparation step further comprises the substeps of:
    a. exposing said absorptive material element to the atmosphere;
    b. placing said absorptive material element in a preparation vessel;
    c. adding an extraction agent to said preparation vessel; and
    d. adding a derivatizing agent to said preparation vessel.

36. The method of claim 35, wherein said purification step comprises at least one of liquid chromatography, gas chromatography, capillary electrophoresis, ion mobility separation, electrospray ionization, matrix assisted laser desorption ionization, direct electrospray ionization, and solvent extraction.

37. The method of claim 35, wherein said analysis step comprises performance of mass spectrometry.

38. The method of claim 35, wherein said derivatizing agent and extraction agent are added in a single step.

39. The method of claim 35, wherein said derivatizing agent reacts with a functional group on the analyte of interest.

40. The method of claim 35, wherein an internal standard is added to said absorptive material element one or more of before the introduction of said sample and after the introduction of said sample.

41. The method of claim 35, wherein isotopically-labeled internal standard is added to said whole blood sample before said sample is introduced to said PSD.

42. A method for determining the presence, concentration, or amount of Vitamin D and its analogs in a plasma sample comprising the steps of:
    a. Collecting, separating, and aliquoting a plasma sample by use of a PSD, wherein said collection reservoir of said PSD comprises an absorptive material element and said aliquoted plasma sample becomes substantially absorbed by said absorptive material element;
    b. Preparing said plasma sample for analysis by at least derivatizing said sample, wherein the derivatizing agent comprises at least one of: 4-(1-methyl-4-pyrindinylmethyl)-1,2,4-triazolidine-3,5-dione, 4-phenyl-1,2,4-triazolidine-3,5-dione, and 4-ferrocenylmethyl-1,2,4-triazolidine-3,5-dione, and their isomers, isotopes, and analogs;
c. Purifying said plasma sample; and
d. Analyzing said plasma sample.

43. The method of claim 42, wherein the preparation step further comprises the substeps of:
a. exposing said absorptive material element to the atmosphere;
b. placing said absorptive material element in a preparation vessel;
c. adding an extraction agent to said preparation vessel; and
d. adding a derivatizing agent to said preparation vessel.

44. The method of claim 43, wherein said purification step comprises at least one of liquid chromatography, gas chromatography, capillary electrophoresis, ion mobility separation, electrospray ionization, matrix assisted laser desorption ionization, direct electrospray ionization, and solvent extraction.

45. The method of claim 43, wherein said analysis step comprises performance of mass spectrometry.

46. The method of claim 43, wherein an isotopically labeled internal standard is added to said sample.

47. The method of claim 5 in which at least one of said one or more internal standards are isotopically tagged.

48. The method of claim 15 in which at least one of said one or more internal standards are isotopically tagged.

49. The method of claim 26 in which at least one of said one or more internal standards are isotopically tagged.

* * * * *